United States Patent [19]

Karami

[11] 4,027,672

[45] June 7, 1977

[54] ABSORBENT ARTICLE WITH IMPROVED PAD AND METHOD

[75] Inventor: Hamzeh Karami, Crystal Lake, Ill.

[73] Assignee: Colgate-Palmolive Company, New York, N.Y.

[22] Filed: Dec. 29, 1975

[21] Appl. No.: 644,691

[52] U.S. Cl. .............................. 128/284; 128/287; 128/290 P
[51] Int. Cl.² .................... A61F 13/16; B32B 5/12
[58] Field of Search .......... 428/218, 139, 137, 170; 128/284, 287, 290 R, 290 P, 290 W, 296

[56] References Cited

UNITED STATES PATENTS

| | | | |
|---|---|---|---|
| 2,788,003 | 4/1957 | Morin | 128/284 |
| 3,544,420 | 12/1970 | Murphy et al. | 128/284 X |
| 3,766,922 | 10/1973 | Krusko | 128/284 |
| 3,897,784 | 8/1975 | Fitzgerald | 128/290 R |
| 3,934,588 | 1/1976 | Mesek | 128/290 W |
| 3,969,561 | 7/1976 | Marshall | 428/113 |

*Primary Examiner*—Aldrich F. Medbery
*Attorney, Agent, or Firm*—Powell L. Sprunger

[57] ABSTRACT

An absorbent article comprising, an absorbent pad assembly having an absorbent pad comprising a mass of fibers. The pad has densified regions for transmitting liquid through the pad at relatively high rates and for supporting the pad when placed under loads. The pad also has relatively undensified areas adjacent the regions to provide a relatively high liquid holding capacity for the pad, with the regions having a thickness approximately at least as large as the thickness of said areas.

21 Claims, 17 Drawing Figures

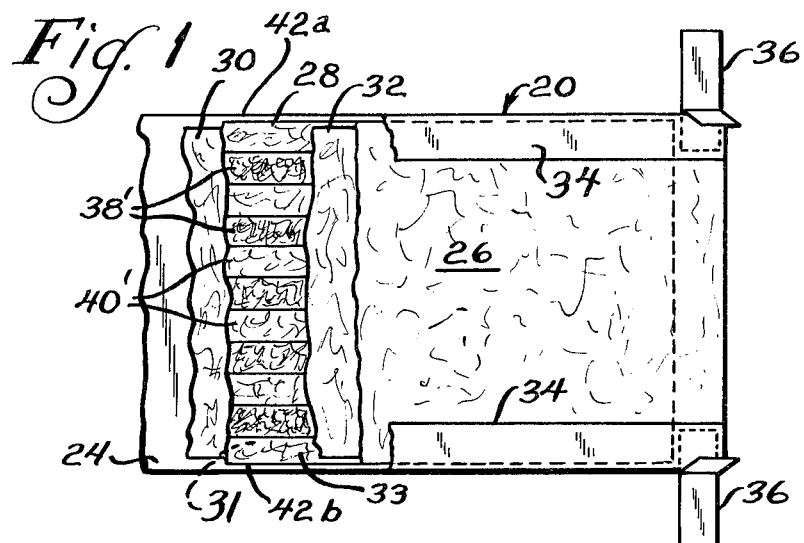
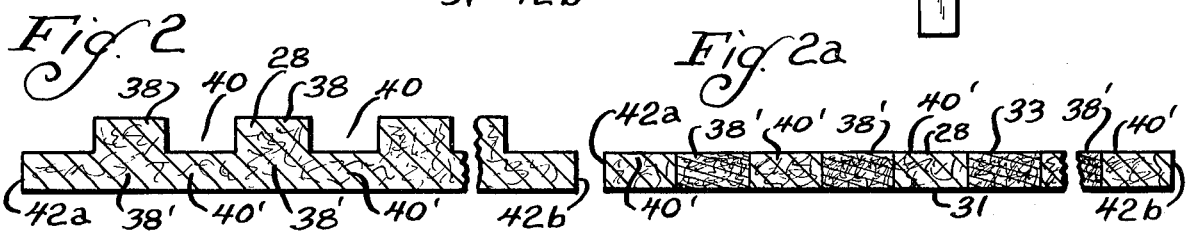
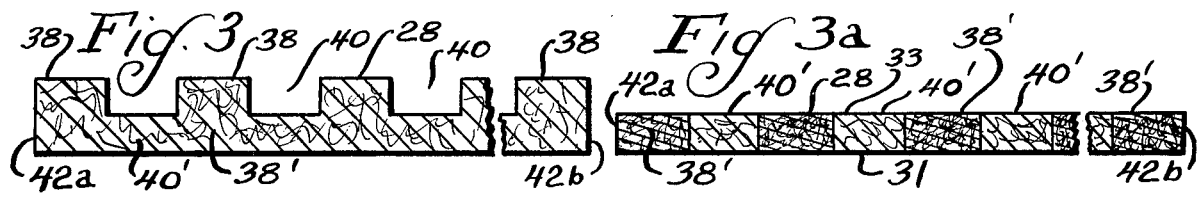
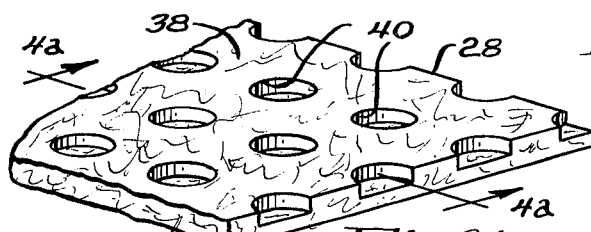
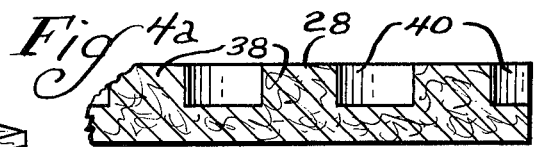
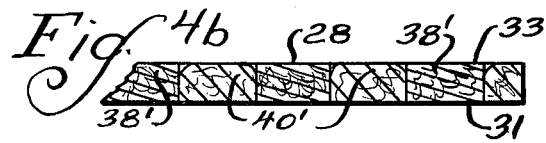
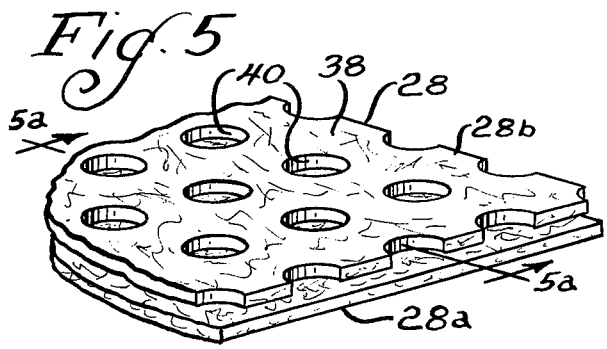
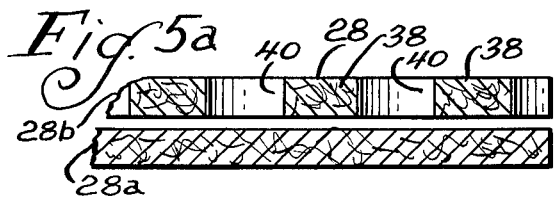
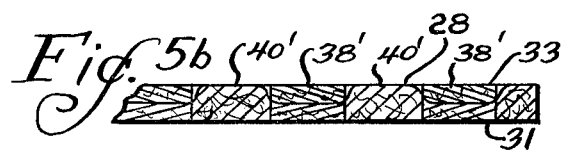

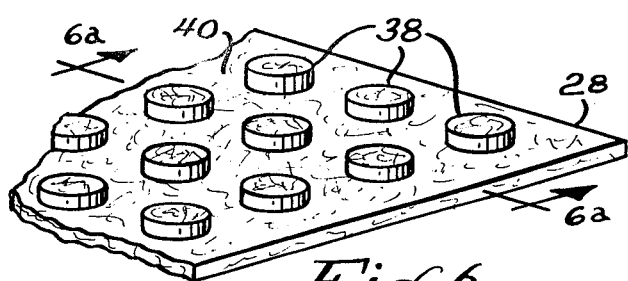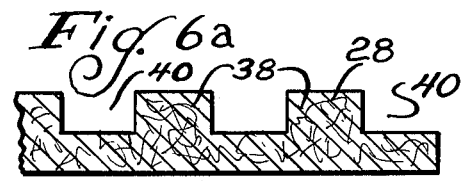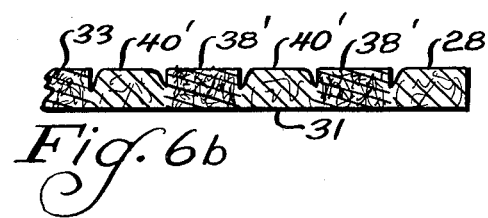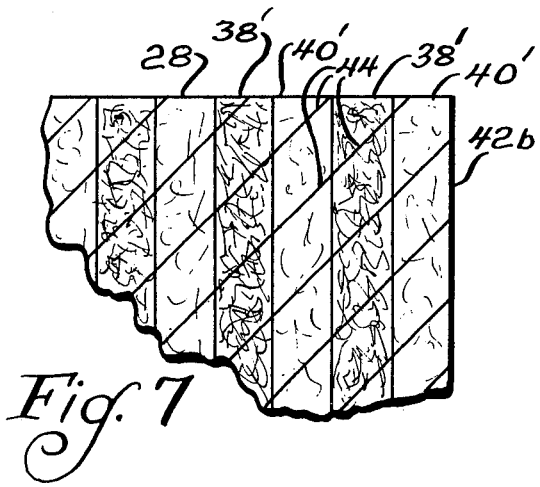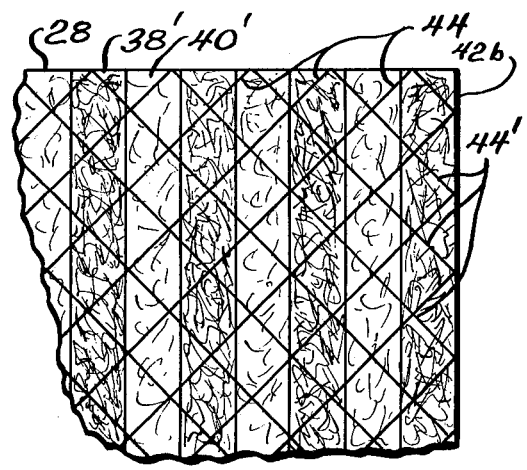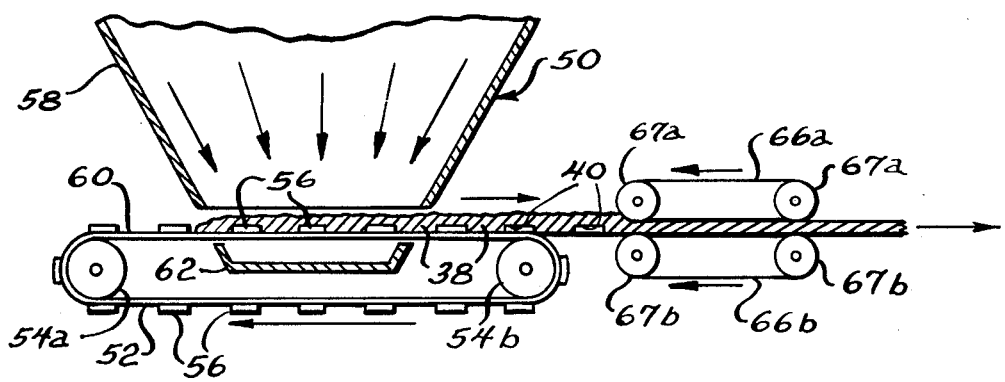

ABSORBENT ARTICLE WITH IMPROVED PAD AND METHOD

BACKGROUND OF THE INVENTION

The present invention relates to absorbent articles, and more particularly to absorbent pads for the articles.

In the past, disposable absorbent articles, such as diapers, have been provided with absorbent pads to receive and retain body fluids. In order for the articles to function in a suitable manner, the pads should be capable of transmitting the body fluids from the point of application to remote areas of the pads, thus distributing the fluids throughout the pads and minimizing saturation at the point of application. In addition, the pads should be capable of retaining the body fluids when the pads are placed under loads, else the fluids will leak from ends of the pads.

Particularly in the case of disposable diapers, the pads are normally made from a mass of fibers, such as comminuted wood pulp known as wood fluff. In large part, the fluid holding capacity of such pads is dependent upon the spacings between the pad fibers, and if the interfiber spacings of the pads are reduced in size, the capability of the pads for retaining fluids is correspondingly lessened. Alternatively, pads having smaller interfiber spacings provide greater fluid absorption and transmission rates than pads having larger interfiber spacings.

Some of the diapers have been made with pads which are compressed to a relatively high degree throughout the pads. Although the pads of such diapers may spread fluid throughout the pads, the diapers are unsatisfactory since their pads are not capable of retaining a sufficient quantity of body fluids, and thus leak. Also, the pads of such diapers are relatively stiff, and do not readily conform to the shape of the infant. Other diapers have been made with pads which are relatively uncompressed throughout the pads, but such pads are not capable of adequately distributing fluids in the pads.

In an attempt to solve these problems, some diapers have been provided with pads which are compressed to a reduced thickness in certain parts of the pads to provide relatively dense and undense portions of the pads. In theory, the compressed parts of the pads should distribute fluids to spaced portions of the pads, while the uncompressed parts of the pads should retain fluids. However, when such pads are placed under loads during use, the pads permit the originally undensified portions of the pads to be compressed, thus significantly reducing the interfiber spacings in the uncompressed parts of the pads. Accordingly, such loaded pad portions are effectively reformed into densified portions, such that the fluid holding capacity of the pads is impaired and resulting in possible leakage from the pads.

SUMMARY OF THE INVENTION

A principal feature of the present invention is the provision of an absorbent article of simplified construction having an improved absorbent pad.

The article of the present invention comprises, an absorbent pad assembly having an absorbent pad comprising a mass of fibers. The pad has densified regions and relatively undensified areas adjacent the regions, with the regions having a thickness approximately at least as large as the thickness of the areas.

A feature of the present invention is that the densified regions transmit liquid to remote portions of the pad at relatively high rates.

Another feature of the invention is that the undensified areas provide a relatively high liquid holding capacity for the pad.

Yet another feature of the invention is that the densified regions transmit liquid to the undensified areas for retention of liquid therein.

Still another feature of the invention is that the densified regions support the pad when placed under loads to minimize compression of the undensified areas.

Thus, a feature of the present invention is that the pad has improved liquid distribution and retention characteristics when placed under loads during use.

A further feature of the invention is that the densified regions have a higher cross-sectional weight per unit volume than the corresponding weight of the undensified areas.

A further feature of the invention is that the combination of undensified areas and densified regions provide a pad which is soft and readily conformable to the shape of the wearer.

Yet another feature of the present invention is the provision of a method for making the absorbent articles of the present invention.

Further features will become more fully apparent in the following description of the embodiments of this invention and from the appended claims.

DESCRIPTION OF THE DRAWINGS

In the drawings:

FIG. 1 is a fragmentary plan view of an absorbent article of the present invention being illustrated in the form of a disposable diaper;

FIGS. 2 and 2a are fragmentary sectional views showing one embodiment of an absorbent pad for the article of the present invention before and after compression;

FIGS. 3 and 3a are fragmentary sectional views showing another embodiment of an absorbent pad for the article of the present invention before and after compression;

FIG. 4 is a fragmentary perspective view of another embodiment of an absorbent pad for the article of the present invention;

FIG. 4a is a fragmentary sectional view taken substantially as indicated along the line 4a—4a of FIG. 4;

FIG. 4b is a fragmentary sectional view of the pad of FIGS. 4 and 4a after being compressed;

FIG. 5 is a fragmentary perspective view of another embodiment of an absorbent pad for the article of the present invention;

FIG. 5a is a fragmentary sectional view taken substantially as indicated along the line 5a—5a of FIG. 5;

FIG. 5b is a fragmentary diagrammatic view of the pad of FIGS. 5 and 5a illustrating generally the configuration assumed after being compressed;

FIG. 6 is a fragmentary perspective view of another embodiment of an absorbent pad for the article of the present invention;

FIG. 6a is a fragmentary sectional view taken substantially as indicated along the line 6a—6a of FIG. 6;

FIG. 6b is a fragmentary sectional view of the pad of FIGS. 6 and 6a after being compressed;

FIGS. 7 and 8 are fragmentary plan views of additional embodiments of absorbent pads for the article of the present invention; and FIG. 9 is a diagrammatic view showing an apparatus for constructing absorbent pads according to a method of the present invention.

DESCRIPTION OF THE PREFERRED EMBODIMENTS

Referring now to FIG. 1, there is shown an absorbent article generally designated 20. Although the absorbent article of the present invention is useful for many purposes, such as sanitary pads and maternity napkins, the article will be described in the form of a disposable diaper for convenience. The article or diaper 20 has an absorbent pad assembly 22 having a fluid impervious backing sheet 24 defining a back surface of the diaper, a fluid pervious top or cover sheet 26 defining a substantial portion of a front surface of the diaper, and an absorbent pad 28 positioned between the backing sheet 24 and top sheet 26. The diaper 20 may have a back wadding sheet 30 positioned beneath a back surface 31 of the pad 28, and a front wadding sheet 32 positioned against a front surface 33 of the pad 28. The back and front wadding sheets 30 and 32 provide structural integrity for the pad 28 and prevent balling of the pad during use of the diaper. As shown, the backing sheet 24 may have lateral side margins 34 folded over and secured to the top sheet 26 above the pad 28. Also, the diaper may have a pair of conventional tape fasteners 36 for use in securing the diaper about an infant during placement of the diaper.

The pad 28 may be made of a mass of fibers, such as comminuted wood pulp, known as wood fluff. Referring to FIG. 2, the pad 28 is initially formed with a plurality of raised strips 38 extending longitudinally in the pad 28. The raised strips 38 are spaced from each other and define elongated openings 40 extending longitudinally in the pad between the strips 38 and extending partially through the thickness of the pad 28. Thus, the pad of FIG. 2 has relatively thick regions 38' which include the strips 38, and relatively thin areas 40' located beneath the openings 40 and between the regions 38'. As will be further described below, the irregular pad of FIG. 2 is compressed to form a pad having a substantially uniform thickness throughout the pad, as shown in FIG. 2a. Since the initial pad of FIG. 2 has a greater thickness in the regions 38', the regions 38' in the compressed pad of FIG. 2a are compressed to a much greater extent than the areas 40' which may be slightly compressed or uncompressed. Thus, the compressed pad of FIG. 2a has a plurality of longitudinally extending regions 38' which are highly densified due to compression in these regions, with the regions 38' being separated by longitudinally extending areas 40' which are relatively undensified.

With reference to FIG. 2a, the fibers in the densified regions 38' are closely pressed together, thus reducing the interfiber spaces in the densified regions to a small size, while the fibers in the undensified areas 40' define relatively large interfiber spaces. Since the interfiber spaces in the densified regions 38' are relatively small, the densified regions 38' rapidly absorb liquid from the front of the diaper and transmit the liquid to portions of the diaper remote the point of application to the diaper. Since the fibers in the undensified areas 40' define relatively large interfiber spacings, the undensified areas 40' provide the pad with localities having relatively large liquid holding capacities. Thus, the liquid is transmitted by the densified regions 38' to the undensified areas 40' where the liquid is retained in the pad.

Although in a preferred form the densified regions 38' of the compressed pad have approximately the same thickness as the undensified areas 40', it will be apparent that the densified regions 38' may have a greater thickness than the undensified areas, if desired. In both cases, the densified regions 38' are sufficiently thick to provide support for the pad when placed under loads during use, and minimize compression of the undensified areas 40' when the pad is placed under loads. Thus, the densified regions 38' serve to maintain the interfiber spacings of the undensified areas 40' open during use of the diaper to prevent degradation of fluid holding capacity in these areas. It will be apparent that the densified regions 38' of the compressed pad have a greater weight per unit volume of cross-section extending between the front and back surfaces 33 and 31 of the pad than the undensified areas 40'.

Referring to FIG. 2, in the present embodiment the strips 38 are spaced from side edges 42a and 42b of the pad 28, such that the compressed pad 28 of FIGS. 1 and 2a has undensified areas 40' located adjacent the side edges 42a and b of the pad, while the densified regions 38' are spaced from the side edges of the pad. Alternatively, as shown in FIG. 3, the pad 28 may have longitudinal strips 38 located adjacent the side edges 42a and b of the pad 28, such that densified regions 38' are formed at the side edges 42a and b of the pad 28, as shown in FIG. 3a. Additionally, as illustrated in FIG. 7, the pad 28 may be further compressed along lines of embossing 44 which connect spaced densified regions 38' and undensified areas 40'. The lines of embossing 44 reduce the size of the interfiber spacings in limited portions of the undensified areas 40', and serve to rapidly transmit liquid between separate densified regions 38' across the undensified areas 40'. In the embodiment shown in FIG. 7, lines of embossing 44' are formed diagonally relative side edges of the pad 28, although they may be formed at any suitable angle, and may include additional lines of embossing 44', as shown in FIG. 8, which cross the lines of embossing 44 to form a diamond-shaped pattern in the pad 28. Of course, the lines of embossing may be included in any of the embodiments of the present invention. Also, the absorbent pads described above may be turned 90° in order to position the undensified areas and densified regions with the strips extending laterally or transversely in the pad assembly.

Another embodiment of the present invention is illustrated in FIGS. 4, 4a, and 4b, in which like reference numerals designate like parts. With reference to FIGS. 4 and 4a, in this embodiment the pad 28 initially has a plurality of circularshaped openings 40 extending partially through the pad and defining raised portins 38 of the pad surrounding the openings 40. Referring to FIG. 4b, when the pad 28 is compressed, the densified regions 38' of the compressed pad are formed corresponding to the raised regions 38 of the initial pad, while the undensified areas 40' are formed in the pad beneath the openings 40 of the initial pad. The undensified areas 40' thus have an approximately circular shape, while the densified regions 38' surround the undensified areas 40'. Of course, the undensified areas 40' may have any suitable shape, as desired. The densified regions 38' serve to rapidly absorb and transmit liquid throughout the compressed pad 28 and to support the diaper when placed under loads, while the undensified areas 40' serve to retain liquid in the pad, as previously described.

Another embodiment of the present invention is illustrated in FIGS. 5, 5a, and 5b, in which like reference numerals designate like parts. Referring to FIGS. 5 and 5a, the pad 28 has a first pad layer 28a of uniform thickness, and a second pad layer 28b positioned against the first pad layer 28a. The second pad layer 28b has a plurality of openings 40 extending through the second pad layer 28b and defining regions 38 of the second pad layer 28b surrounding the openings 40. With reference to FIG. 5b, when the first and second pad layers 28a and b are suitably compressed, the resulting pad 28 has densified regions 38' which correspond to the regions 38 of additional pad material in the second pad layer 28b and has undensified areas 40' defined by the material of the first pad layer 28a beneath the openings 40 of the second pad layer 28b. Thus, the undensified areas 40' have a substantially circular shape, although these areas may be made of any suitable shape, as desired. The densified regions 38' and undensified areas 40' of the compressed pad of FIG. 5b cooperate in a manner as previously described in connection with the pads of FIGS. 1–4b.

Another embodiment of the present invention is illustrated in FIGS. 6, 6a, and 6b, in which like reference numerals designate like parts. Referring to FIGS. 6 and 6a, the initial pad 28 has a plurality of raised circular regions 38 and recessed areas 40 surrounding the raised regions 38. With reference to FIG. 6b, when the pad 28 is suitably compressed, the densified regions 38' correspond to the initial raised regions 38 and have a circular shape, while the undensified areas 40 surround the densified regions 38'. Of course, the densified regions 38' may have any suitable shape, as desired. The compressed pad 28 of FIG. 6b operates in a manner as previously described in connection with the other pads of the present invention.

An apparatus generally designated 50 is illustrated in FIG. 9 for making absorbent pads according to a method of the present invention. The apparatus 50 has an endless screen 52 supported by a pair of rollers 54a and 54b and driven by the rollers in a clockwise direction, as shown. The screen 52 has a plurality of blocks 56 secured to the outside of the screen, such that the blocks cover areas of the screen on which they are retained. The blocks 52 may have any suitable shape, such as a generally cylindrical configuration. The apparatus has a chute 58 supported above an upper reach 60 of the screen 52 for depositing fibers, such as comminuted wood pulp, onto the upper reach 60 of the screen 52. The apparatus 50 also has a plate 62 located beneath the upper reach 60 of the screen 52 and beneath the chute 58, with the plate 62 being connected to a vacuum source in order to assist deposition of the fibers passing from the chute 58 onto the upper reach 60 of the screen 52.

In operation, the vacuum plate 62 and chute 58 cooperate to form a layer of wood fluff on the upper reach 60 of the screen 52, while the blocks 56 prevent passage of air through the screen 52 and reduce buildup of fluff in the areas of the blocks 56. Accordingly, a layer of fluff is formed having a plurality of openings 40 in the lower part of the fluff layer corresponding to the location of the blocks, and having raised regions 38 between the location of the openings 40. The layer of fluff passes from the upper reach 60 of the screen 52 towards a pair of endless belts 66a and 66b, supported and driven by respective pairs of rollers 67a and 67b, where the layer of fluff is compressed into a web 70 when the layer passes between the belts 66a and b. Thus, the resulting web 70 has undensified areas corresponding to the locations of the openings 40, and densified regions surrounding the undensified areas corresponding to the locations of the raised regions 38. The compressed web 70 may be cut into lengths and formed into pads for the absorbent articles either in the orientation shown or by inverting the web 70, as desired.

In accordance with a method of the present invention, the absorbent articles are made by forming an absorbent pad having a plurality of spaced openings extending partially through the thickness of the pad. The pad is compressed to define densified regions of the pad located between the openings and relatively undensified areas in the locality of the openings.

The foregoing detailed description is given for clearness of understanding only, and no unnecessary limitations should be understood therefrom, as modifications will be obvious to those skilled in the art.

I claim:

1. An absorbent article comprising, an absorbent pad assembly having a backing sheet of fluid impervious material, a top sheet, and an absorbent pad located intermediate the backing and top sheets and comprising a mass of fibers, said pad having densified regions for transmitting liquid through the pad at relatively high rates and for supporting the pad when placed under loads, and relatively undensified areas adjacent said regions providing a relatively high liquid holding capacity for the pad, with said regions having a thickness approximately at least as large as the thickness of said areas.

2. The article of claim 1 wherein said regions are separated by said areas.

3. The article of claim 2 wherein said regions have a generally circular shape.

4. The article of claim 1 wherein said areas are separated by said regions.

5. The article of claim 4 wherein said areas have a generally circular shape.

6. The article of claim 1 wherein said areas and regions comprise elongated strips, with said areas and regions separating each other in the pad.

7. The article of claim 1 wherein said regions comprise a plurality of longitudinally extending spaced strips in the pad, and said areas comprise a plurality of longitudinally extending strips separating said regions.

8. The article of claim 7 wherein a pair of said regions are located adjacent opposed side edges of the pad.

9. The article of claim 7 wherein a pair of said areas are located adjacent opposed side edges of the pad.

10. The article of claim 1 wherein said article comprises a disposable diaper.

11. The article of claim 1 wherein said regions have a thickness approximately equal to the thickness of said areas.

12. The article of claim 1 including lines of embossing in said pad connecting spaced regions of the pad.

13. The article of claim 1 including lines of embossing in said pad connecting spaced areas of the pad.

14. The article of claim 1 wherein said regions comprise a plurality of laterally extending spaced strips in the pad, and said areas comprise a plurality of laterally extending strips separating said regions.

15. An absorbent article comprising, an absorbent pad assembly having an absorbent pad comprising a mass of fibers, said pad having relatively uncompressed areas providing relatively large interfiber spaces between the fibers for enhanced liquid holding capacity in said areas, and said pad having regions adjacent said areas which are compressed to a thickness approximately at least as large as the thickness of the areas, said regions supporting the pad when placed under loads and providing interfiber spaces of reduced size for rapidly transmitting liquid from the regions to said areas and retention therein.

16. An absorbent article comprising, an absorbent pad assembly having a backing sheet of fluid impervious material, a fluid previous top sheet, and an absorbent pad located intermediate said backing and top sheets, said pad having a front surface, a back surface, relatively densified regions, and relatively undensified areas adjacent said regions, said pad regions having a greater weight per unit volume of cross-section extending between said front and back surfaces than the corresponding weight of said pad areas.

17. A method of making an absorbent article comprising, forming an absorbent pad assembly having an absorbent pad comprising a mass of fibers, with said pad having regions of initial thickness greater than adjacent areas of the pad, and compressing said regions to a thickness approximately at least as large as the thickness of said areas in the compressed pad, said areas providing relatively high liquid holding capacity for the pad, and said regions transmitting liquid to said areas at a relatively high rate and supporting the pad when placed under loads.

18. A method of making an absorbent article comprising, forming an absorbent pad assembly having an absorbent pad, with said pad having a plurality of openings extending partially through the pad defining areas of reduced thickness and raised regions of the pad adjacent said areas, and compressing said pad to a substantially uniform thickness to densify said regions relative said areas.

19. A method of making an absorbent article comprising, forming an absorbent pad assembly having a first absorbent pad layer, and a second absorbent pad layer having a plurality of spaced openings extending through the second layer and positioned against the first layer, and compressing said first and second pad layers to define densified regions located between the openings and relatively undensified areas in the locality of the openings.

20. A method of making an absorbent article comprising the steps of:
 forming an absorbent pad having a plurality of spaced openings extending partially through the thickness of the pad; and
 compressing the pad to define densified regions of the pad located between the openings and relatively undensified areas in the locality of the openings.

21. The method of claim 20 wherein said compressing step compresses the pad to a substantially uniform thickness throughout the pad.

* * * * *